United States Patent
Snell et al.

(10) Patent No.: US 10,736,619 B2
(45) Date of Patent: Aug. 11, 2020

(54) BONE IMPLANT WITH CONVERTIBLE SUTURE ATTACHMENT

(71) Applicant: Tornier, Inc., Bloomington, MN (US)

(72) Inventors: Douglas B. Snell, Saint Ismier (FR); Daniel E. Morgan, Salem, MA (US); Daniel J. Yasevac, Somerville, MA (US); Justin C. Anderson, Spring Park, MN (US)

(73) Assignee: Tornier, Inc., Bloomington, MN (US)

( * ) Notice: Subject to any disclaimer, the term of this patent is extended or adjusted under 35 U.S.C. 154(b) by 859 days.

(21) Appl. No.: 15/188,234

(22) Filed: Jun. 21, 2016

(65) Prior Publication Data
US 2016/0296224 A1 Oct. 13, 2016

Related U.S. Application Data

(63) Continuation of application No. 13/510,240, filed as application No. PCT/US2010/056883 on Nov. 16, 2010, now Pat. No. 9,445,805.
(Continued)

(30) Foreign Application Priority Data

Feb. 11, 2010 (FR) .................................... 10 50965

(51) Int. Cl.
*A61B 17/04* (2006.01)
*A61B 90/00* (2016.01)

(52) U.S. Cl.
CPC .. *A61B 17/0401* (2013.01); *A61B 2017/0409* (2013.01); *A61B 2017/0412* (2013.01);
(Continued)

(58) Field of Classification Search
CPC ........ A61B 17/0401; A61B 2017/0409; A61B 2017/0412; A61B 2017/0414; A61B 2017/0422; A61B 2017/0438
See application file for complete search history.

(56) References Cited

U.S. PATENT DOCUMENTS

| 1,562,543 A | 11/1925 | Cox |
| 3,527,223 A | 9/1970 | Shein |

(Continued)

FOREIGN PATENT DOCUMENTS

| EP | 0 673 624 | 9/1995 |
| EP | 0 713 683 | 5/1996 |

(Continued)

OTHER PUBLICATIONS

Duerig et al., "Metals: Superelastic Nitinol for Medical Devices", Medical Plastics and Biomaterials, Mar. 1997, in 7 pages.
(Continued)

*Primary Examiner* — Julie A Szpira
(74) *Attorney, Agent, or Firm* — Knobbe, Martens, Olson & Bear, LLP

(57) ABSTRACT

Some embodiments of the present invention include a suture anchor with both knotless and knotted suture attachment capabilities, as well as methods for loading the suture in knotless and knotted configurations. Some embodiments of the present invention include a suture anchor with an inner implant body with a spreader that slides in relation to an outer expandable collar, such that pushing the expandable collar distally with an inserter causes the spreader to expand the collar against the surrounding bone to secure the suture anchor in place. Such embodiments may also include a detachment or breakaway feature between the inserter and the suture anchor to permit separation after anchor deployment. Some embodiments of the present invention include methods for deploying such suture anchors and expanding
(Continued)

the expandable collars and/or detaching the inserter tools. Embodiments of the present invention may be used in various orthopedic applications such as, for example, shoulder repair.

20 Claims, 8 Drawing Sheets

Related U.S. Application Data

(60) Provisional application No. 61/261,480, filed on Nov. 16, 2009.

(52) U.S. Cl.
CPC ............ A61B 2017/0414 (2013.01); A61B 2017/0422 (2013.01); A61B 2017/0438 (2013.01); A61B 2017/0445 (2013.01); A61B 2017/0448 (2013.01); A61B 2017/0451 (2013.01); A61B 2017/0459 (2013.01); A61B 2090/037 (2016.02)

(56) References Cited

U.S. PATENT DOCUMENTS

| | | |
|---|---|---|
| 3,716,058 A | 2/1973 | Tanner, Jr. |
| 4,170,990 A | 10/1979 | Baumgart et al. |
| 4,485,816 A | 12/1984 | Krumme |
| 4,632,100 A | 12/1986 | Somers et al. |
| 4,665,906 A | 5/1987 | Jervis |
| 4,669,473 A | 6/1987 | Richards et al. |
| 4,870,957 A | 10/1989 | Goble et al. |
| 4,898,156 A | 2/1990 | Gatturna et al. |
| 4,946,468 A | 8/1990 | Li |
| 5,002,550 A | 3/1991 | Li |
| 5,035,712 A | 7/1991 | Hoffman |
| 5,046,513 A | 9/1991 | Gatturna et al. |
| 5,141,520 A | 8/1992 | Goble et al. |
| 5,190,546 A | 3/1993 | Jervis |
| 5,192,303 A | 3/1993 | Gatturna et al. |
| 5,258,016 A | 11/1993 | DiPoto et al. |
| 5,268,001 A | 12/1993 | Nicholson et al. |
| 5,318,579 A | 6/1994 | Chow |
| 5,356,413 A | 10/1994 | Martins et al. |
| 5,358,511 A | 10/1994 | Gatturna et al. |
| 5,372,599 A | 12/1994 | Martins |
| 5,383,905 A | 1/1995 | Golds et al. |
| 5,391,173 A | 2/1995 | Wilk |
| 5,403,348 A | 4/1995 | Bonutti |
| 5,417,712 A | 5/1995 | Whittaker et al. |
| 5,486,197 A | 1/1996 | Le et al. |
| 5,505,735 A | 4/1996 | Li |
| 5,522,820 A | 6/1996 | Gaspari et al. |
| 5,522,845 A | 6/1996 | Wenstrom, Jr. |
| 5,527,343 A | 6/1996 | Bonutti |
| 5,554,171 A | 9/1996 | Gatturna et al. |
| 5,571,104 A | 11/1996 | Li |
| 5,584,835 A | 12/1996 | Greenfield |
| 5,601,557 A | 2/1997 | Hayhurst |
| 5,626,612 A | 5/1997 | Bartlett |
| 5,645,553 A | 7/1997 | Kolesa et al. |
| 5,647,874 A | 7/1997 | Hayhurst |
| 5,649,963 A | 7/1997 | McDevitt |
| 5,662,654 A | 9/1997 | Thompson |
| 5,662,657 A | 9/1997 | Carn |
| 5,681,352 A | 10/1997 | Clancy, III et al. |
| 5,702,397 A * | 12/1997 | Goble .............. A61B 17/0401 606/232 |
| 5,725,557 A | 3/1998 | Gatturna et al. |
| 5,766,218 A | 6/1998 | Arnott |
| 5,843,127 A | 12/1998 | Li |
| 5,876,434 A | 3/1999 | Flomenblit et al. |
| 5,893,856 A | 4/1999 | Jacob et al. |
| 5,948,001 A | 9/1999 | Larsen |
| 5,957,953 A | 9/1999 | DiPoto et al. |
| 5,964,770 A | 10/1999 | Flomenbilt et al. |
| 5,968,078 A | 10/1999 | Grotz |
| 5,972,000 A | 10/1999 | Beyar et al. |
| 5,980,558 A | 11/1999 | Wiley |
| 5,984,927 A | 11/1999 | Wenstrom, Jr. et al. |
| 6,027,523 A | 2/2000 | Schmieding |
| 6,033,430 A | 3/2000 | Bonutti |
| 6,042,583 A | 3/2000 | Thompson et al. |
| 6,066,160 A | 5/2000 | Colvin et al. |
| 6,077,216 A | 6/2000 | Benderev et al. |
| 6,113,611 A | 9/2000 | Allen et al. |
| 6,146,406 A * | 11/2000 | Shluzas .............. A61B 17/0401 606/232 |
| 6,200,330 B1 | 3/2001 | Benderev et al. |
| 6,210,413 B1 | 4/2001 | Justis et al. |
| 6,287,325 B1 | 9/2001 | Bonutti |
| 6,299,448 B1 | 10/2001 | Zdrahala et al. |
| 6,328,758 B1 | 12/2001 | Tornier et al. |
| 6,334,446 B1 | 1/2002 | Beyar |
| 6,387,041 B1 | 5/2002 | Harari et al. |
| 6,406,480 B1 | 6/2002 | Beyar et al. |
| 6,447,524 B1 | 9/2002 | Knodel et al. |
| 6,451,024 B1 | 9/2002 | Thompson et al. |
| 6,527,774 B2 | 3/2003 | Lieberman |
| 6,544,273 B1 | 4/2003 | Harari et al. |
| 6,585,730 B1 * | 7/2003 | Foerster .............. A61B 17/0401 411/80 |
| 6,635,058 B2 | 10/2003 | Beyar et al. |
| 6,656,183 B2 | 12/2003 | Colleran et al. |
| 6,663,642 B2 | 12/2003 | Beyar et al. |
| 6,692,516 B2 * | 2/2004 | West, Jr. ............ A61B 17/0401 606/232 |
| 6,730,110 B1 | 5/2004 | Harari et al. |
| 6,746,455 B2 | 6/2004 | Beyar et al. |
| 6,770,076 B2 | 8/2004 | Foerster |
| 6,773,437 B2 | 8/2004 | Ogilvie et al. |
| 6,855,157 B2 | 2/2005 | Foerster |
| 6,960,160 B2 | 11/2005 | Browning |
| 6,986,781 B2 | 1/2006 | Smith |
| 7,083,638 B2 | 8/2006 | Foerster |
| 7,090,690 B2 | 8/2006 | Foerster et al. |
| 7,309,337 B2 | 12/2007 | Colleran et al. |
| 7,744,613 B2 | 6/2010 | Ewers et al. |
| 7,938,847 B2 | 5/2011 | Fanton et al. |
| 8,100,940 B2 | 1/2012 | Leung et al. |
| 8,118,835 B2 | 2/2012 | Weisel et al. |
| 8,292,932 B2 | 10/2012 | Matthis et al. |
| 8,721,650 B2 | 5/2014 | Fanton et al. |
| 8,758,406 B2 * | 6/2014 | Fanton ............... A61B 17/0401 606/232 |
| 9,089,323 B2 * | 7/2015 | Bonutti ............. A61B 17/0487 |
| 9,445,805 B2 | 9/2016 | Snell et al. |
| 9,539,001 B2 | 1/2017 | Fanton et al. |
| 10,016,192 B2 | 7/2018 | Beck |
| 2001/0051816 A1 | 12/2001 | Enzerink et al. |
| 2002/0082622 A1 | 6/2002 | Kane |
| 2002/0111653 A1 * | 8/2002 | Foerster ............. A61B 17/0401 606/232 |
| 2003/0078465 A1 | 4/2003 | Pai et al. |
| 2003/0088272 A1 | 5/2003 | Smith |
| 2003/0120309 A1 | 6/2003 | Colleran et al. |
| 2004/0078054 A1 | 4/2004 | Biggs et al. |
| 2004/0098050 A1 | 5/2004 | Foerster et al. |
| 2004/0220617 A1 | 11/2004 | Pedlick et al. |
| 2004/0236170 A1 | 11/2004 | Kim |
| 2004/0260317 A1 | 12/2004 | Bloom et al. |
| 2004/0267275 A1 | 12/2004 | Cournoyer et al. |
| 2005/0080454 A1 | 4/2005 | Drews et al. |
| 2005/0187555 A1 | 8/2005 | Biedermann et al. |
| 2005/0245932 A1 | 11/2005 | Fanton et al. |
| 2006/0036244 A1 | 2/2006 | Spitler et al. |
| 2006/0089525 A1 | 4/2006 | Mamo et al. |
| 2006/0100630 A1 | 5/2006 | West, Jr. |
| 2006/0106422 A1 | 5/2006 | Del Rio et al. |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2007/0156149 A1 | 7/2007 | Fanton et al. |

(56) References Cited

U.S. PATENT DOCUMENTS

| | | | |
|---|---|---|---|
| 2007/0156150 A1 | 7/2007 | Fanton et al. | |
| 2007/0156176 A1 | 7/2007 | Fanton et al. | |
| 2007/0255317 A1* | 11/2007 | Fanton | A61B 17/062 606/232 |
| 2008/0275469 A1* | 11/2008 | Fanton | A61B 17/0401 606/139 |
| 2010/0292732 A1 | 11/2010 | Hirotsuka et al. | |
| 2011/0264141 A1 | 10/2011 | Denham et al. | |
| 2011/0313453 A1* | 12/2011 | Krumme | A61B 17/0401 606/232 |
| 2012/0290004 A1 | 11/2012 | Lombardo et al. | |
| 2014/0371792 A1 | 12/2014 | Beck | |
| 2015/0182213 A1 | 7/2015 | Gelfand et al. | |

FOREIGN PATENT DOCUMENTS

| | | |
|---|---|---|
| EP | 0 838 197 | 4/1998 |
| EP | 1 820 462 | 8/2007 |
| FR | 2 731 610 | 9/1996 |
| FR | 2 736 254 | 1/1997 |
| JP | H09 75374 | 3/1997 |
| WO | WO 94/28799 | 12/1994 |
| WO | WO 96/39948 | 12/1996 |
| WO | WO 97/30649 | 8/1997 |
| WO | WO 98/010693 | 3/1998 |
| WO | WO 98/11829 | 3/1998 |
| WO | WO 99/22648 | 5/1999 |
| WO | WO 00/035355 | 6/2000 |
| WO | WO 01/054586 | 8/2001 |
| WO | WO 2005/074827 | 8/2005 |
| WO | WO 2005/102190 | 11/2005 |
| WO | WO 2005/122954 | 12/2005 |
| WO | WO 2006/037131 | 4/2006 |
| WO | WO 2007/140309 | 12/2007 |
| WO | WO 2008/109087 | 9/2008 |
| WO | WO 2014/031578 | 2/2014 |

OTHER PUBLICATIONS

International Search Report and Written Opinion issued in PCT Application No. PCT/US2010/056883, dated Mar. 2, 2011, in 14 pages.

Office Action issued in European Patent Application No. 10782499.7, dated Jan. 27, 2015, in 4 pages.

* cited by examiner

BONE IMPLANT WITH CONVERTIBLE SUTURE ATTACHMENT

CROSS-REFERENCE TO RELATED APPLICATIONS

This application is a continuation of U.S. patent application Ser. No. 13/510,240, filed Sep. 22, 2012, which is a national stage application under 35 U.S.C. § 371 of PCT Application No. PCT/US2010/056883, filed Nov. 16, 2010 which claims the benefit of U.S. Provisional Patent Application Ser. No. 61/261,480, filed on Nov. 16, 2009, and claims foreign priority to French Patent Application No. 1050965, filed on Feb. 11, 2010, each of which are incorporated by reference herein in their entireties for all purposes.

TECHNICAL FIELD

Embodiments of the present invention relate generally to suture anchors for bone implantation, and more specifically to suture anchors with multiple kinds of anchoring capabilities.

BACKGROUND

An orthopedic surgery may involve different kinds of repairs within the same procedure. For example, an operation to repair shoulder instability may include capsular shifts, labral reattachments, or some combination of the two activities. In some cases, a simple knotted suture anchor may provide a desired solution, while in other cases, a more elegant, knotless suture anchor may better accomplish the surgeon's purposes. Existing suture anchors for implantation into bone are typically either for use with knotted sutures or for use with a knotless suture anchoring technique, but not both. However, the particular suture anchoring requirements may not become apparent until after a surgical procedure has begun.

SUMMARY

Some embodiments of the present invention include a suture anchor with both knotless and knotted suture attachment capabilities, as well as methods for loading the suture in knotless and knotted configurations. Some embodiments of the present invention include a suture anchor with an inner implant body with an inverted wedge or spreader that slides in relation to an outer expandable collar, such that pushing the expandable collar distally with an inserter causes the spreader to expand the collar against the surrounding bone to secure the suture anchor in place. Such embodiments may also include a detachment or breakaway feature between the inserter and the suture anchor to permit separation after anchor deployment. Some embodiments of the present invention include methods for deploying such suture anchors and expanding the expandable collars and/or detaching the inserter tools. Embodiments of the present invention may be used in various orthopedic applications such as, for example, shoulder repair.

Example 1. A suture anchoring system according to embodiments of the present invention includes an implant body extending substantially longitudinally from a proximal end to a distal end, the implant body including an insertion nose at the distal end, the insertion nose configured for insertion into bone, a slot formed in the implant body, the slot extending at least partially longitudinally, the slot having a slot proximal edge and a slot distal edge, and a slider that slides along the slot, the slider comprising a slider proximal edge and a slider distal edge, a first aperture at least partially formed by the slot distal edge and the slider distal edge, and a second aperture at least partially formed by the slot proximal edge and the slider proximal edge, the second aperture located proximally with respect to the first aperture, wherein the slider is configured to slide along the slot both before and after implantation of the implant body, such that a suture passed through only one of the first and second apertures before implantation is moveable freely in both directions after implantation, and such that a suture threaded, before implantation, through one of the first and second apertures, around the slider, and back through the other of the first and second apertures is, after implantation, moveable freely in a first direction but substantially inhibited from moving in a second direction opposite the first direction.

Example 2. The suture anchoring system of Example 1, wherein when a suture is threaded through one of the first and second apertures, around the slider, and back through the other of the first and second apertures, the suture moves freely in the first direction, but is pinched between the slider and the slot when moved in the second direction.

Example 3. The suture anchoring system of any of Examples 1 or 2, further including a collar slidably coupled with the implant body, the collar including one or more anchor fins, the collar slideable with respect to the implant body between at least an implant position in which the one or more anchor fins have a maximum lateral dimension smaller than or the same as that of the insertion nose, and a deployed position in which the maximum lateral dimension is larger than that of the insertion nose.

Example 4. The suture anchoring system of any of Examples 1 to 3, wherein the implant body includes a spreader configured to move the one or more anchor fins between the implant position and the deployed position as the collar is slid with respect to the implant body.

Example 5. The suture anchoring system of any of Examples 1 to 4, wherein a proximal end of the spreader is narrower than a distal end of the spreader, such that sliding the collar distally with respect to the implant body moves the collar from the implant position to the deployed position.

Example 6. The suture anchoring system of any of Examples 1 to 5, further including an inserter attachment coupled to the proximal end of the implant body with a break-away coupling.

Example 7. The suture anchoring system of any of Examples 1 to 6, further including an inserter having an outer lateral dimension at its distal end that is smaller than or the same as that of the insertion nose, the inserter coupled to the inserter attachment in a manner which permits actuation of the inserter to slide the collar with respect to the implant body.

Example 8. The suture anchoring system of any of Examples 1 to 7, wherein the inserter includes an outer shaft and an inner shaft, wherein the outer shaft slides with respect to the inner shaft, wherein the inner shaft is rigidly coupled to the inserter attachment, and wherein the outer shaft is configured to abut a proximal end of the collar.

Example 9. The suture anchoring system of any of Examples 1 to 7, wherein the inserter includes an outer shaft configured to receive the inserter attachment, wherein the outer shaft slides with respect to inserter attachment.

Example 10. The suture anchoring system of any of Examples 1 to 9, wherein the inserter is configured to decouple the inserter attachment from the proximal end of the implant body at the break-away coupling by moving the collar from the implant position to the deployed position.

Example 11. The suture anchoring system of any of Examples 1 to 10, further including a loader which includes an inner cavity configured to receive the implant body (or alternatively, both the distal end of the inserter and the implant body), an outer surface, an opening formed in the loader, the opening extending from the outer surface to the inner cavity, wherein the opening has a first opening area at the outer surface and a second opening area at the inner cavity, the first opening area being larger than the second opening area, and an alignment feature, wherein the alignment feature is configured to align one of the first and second apertures with the second opening area when the distal end of the inserter and the implant body are received by the inner cavity.

Example 12. The suture anchoring system of any of Examples 1 to 11, wherein the opening is a first opening, the loader further including a second opening formed in the loader, the second opening extending from the outer surface to the inner cavity, wherein the second opening has a third opening area at the outer surface and a fourth opening area at the inner cavity, the third opening area being larger than the fourth opening area, wherein the alignment feature is further configured to align the second opening area with the first aperture and the fourth opening area with the second aperture when the distal end of the inserter and the implant body are received by the inner cavity.

Example 13. The suture anchoring system of any of Example 1 to 12, wherein the first opening area is at least twice as large as the second opening area.

Example 14. A method for suture anchoring according to embodiments of the present invention includes determining, before implanting a suture anchor, whether to employ knotless or knotted suture attachment using the suture anchor, and threading suture through the suture anchor of Example 1 based on the determination, and sliding the suture in at least one direction with respect to the suture anchor after implantation of the suture anchor.

Example 15. The method of Example 14, wherein the determination is a determination to use knotless suture attachment, wherein threading the suture through the suture anchor further includes threading the suture through one of the first and second apertures, around the slider, and back through the other of the first and second apertures.

Example 16. The method of any of Examples 14 and 15, further including passing the suture through a tissue to form a suture loop having two free ends, wherein threading the suture through the suture anchor further includes threading the two free ends through the one of the first and second apertures, around the slider, and back through the other of the first and second apertures.

Example 17. The method of Example 14, wherein the determination is a determination to use knotted suture attachment, wherein threading the suture through the suture anchor further includes threading the suture through only one of the first and second apertures.

Example 18. The method of any of Examples 14 and 17, further including passing the suture through a tissue to form a suture loop having two free ends, wherein threading the suture through the suture anchor further includes threading the two free ends through the only one of the first and second apertures.

Example 19. The method of any one of Examples 14 to 18, wherein the suture anchor further includes a collar slidably coupled with the implant body, the collar including one or more anchor fins, the method further including sliding the collar with respect to the implant body between at least an implant position in which the one or more anchor fins have a maximum lateral dimension smaller than or the same as that of the insertion nose, and a deployed position in which the maximum lateral dimension is larger than that of the insertion nose.

Example 20. The method of any one of Examples 14 to 19, wherein the suture anchor further includes an inserter attachment coupled to the proximal end of the implant body with a break-away coupling, the method further including decoupling the inserter attachment from the implant body at the break-away coupling.

Example 21. The method of any one of Examples 14 to 20, wherein the suture anchor further includes an inserter having an outer lateral dimension at its distal end that is smaller than or the same as that of the insertion nose, the method further including actuating the inserter to slide the collar with respect to the implant body.

Example 22. The method of any one of Examples 14 to 21, wherein the inserter includes an outer shaft and an inner shaft, wherein the inner shaft is rigidly coupled to the inserter attachment, wherein the outer shaft is configured to abut a proximal end of the collar, and wherein actuating the inserter includes pushing the collar distally relative to the implant body with the outer shaft while pulling the implant body proximally relative to the collar with the inner shaft.

Example 23. The method of any one of Examples 14 to 22, wherein the suture anchor further includes the loader of Example 11, and wherein threading the suture through the at least one of the first and second apertures includes inserting the suture through the opening from the outer surface to the inner surface and then through the at least one of the first and second apertures.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
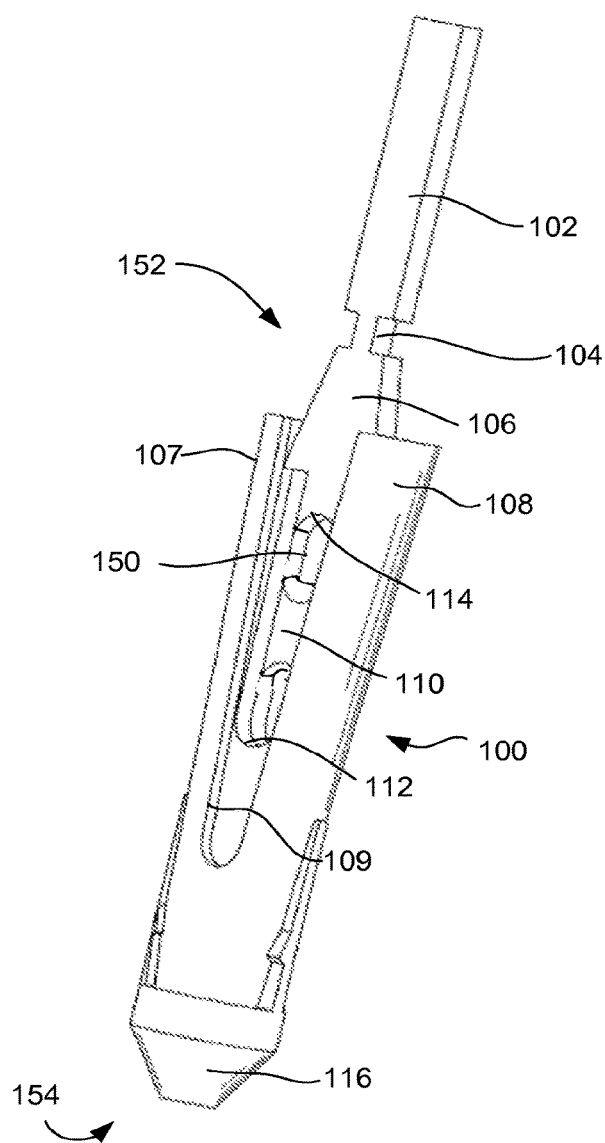
FIG. 1 illustrates a front perspective view of a suture anchor and inserter attachment, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
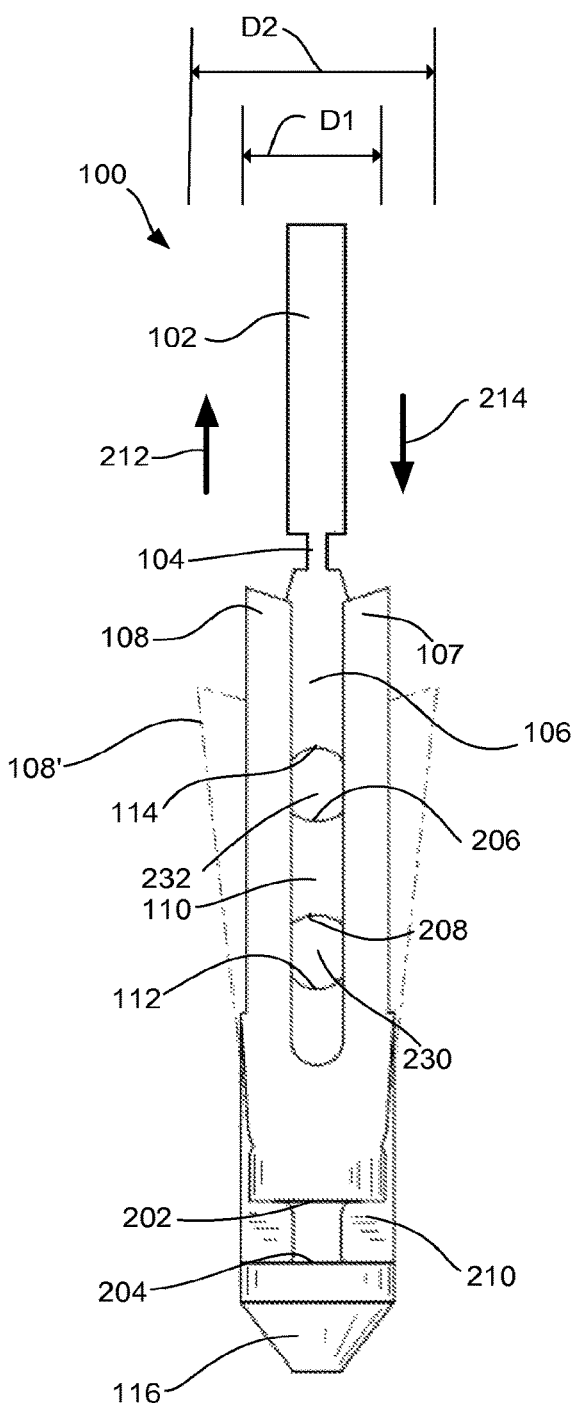
FIG. 2 illustrates a front elevation view of the suture anchor and inserter attachment of FIG. 1, according to embodiments of the present invention.

FIGS. 1 and 2 illustrate a suture anchor 100 and inserter attachment 102 attached to the suture anchor 100, according to embodiments of the present invention. The suture anchor 100 includes an expandable collar 107 which is connected to and slides with respect to an implant body 210. The implant body 210 terminates at its distal end with a conical nose member 116 for insertion into a bone or a bone hole, according to embodiments of the present invention. The proximal end of the implant body 210 includes a spreader 106, which is operatively attached to the inserter attachment 102 by a detachment or breakaway feature 104, according to embodiments of the present invention. A slider 110 slides proximally and distally within, along, or across a notch 150 formed in the implant body 210, between a distal edge 112 and a proximal edge 114 of the notch 150, according to embodiments of the present invention. Notch 150 may also be referred to as slot 150. Slot 150 is formed in the implant body 210 at least partially longitudinally; in other words, at least one component of the slot is in a longitudinal direction, wherein the longitudinal direction is the direction along the length of the implant between the proximal end 152 and distal end 152 of the implant body 210. According to embodiments of the present invention, the implant body 210 includes the nose member 116, the slot 150, and the spreader 106 which are formed as a unitary assembly. According to some embodiments of the present invention, the implant body is constructed (e.g. molded) of a single continuous piece of material.

The spreader 106 is wider at its distal end near edge 114, and narrower at its proximal end near detachment feature 104; this causes the collar 107 to spread or expand when the implant body 210 is moved in the direction indicated by arrow 212 with respect to the collar 107, or when the collar 107 is moved in the direction indicated by arrow 214 with respect to the implant body 210, according to embodiments of the present invention. The collar 107 includes a slot 119 which divides the collar 107 into halves and facilitates the expansion of the collar 107. Each such half may be referred to as an anchor fin 108. In FIG. 2, the fins 108 are depicted in the non-deployed state, while the deployed state of fins is illustrated in dashed lines at reference number 108'. In addition to the spreader 106 sliding proximally with respect to the fins 108 to spread the fins 108, the rest of the implant body 210 also slides proximally with respect to the collar 107 until the bottom 202 of the collar 107 contacts or nears the top of the nose member 116, according to embodiments of the present invention. According to embodiments of the present invention, the furthest proximal extent of the implant body 210 and spreader 106 is limited by the abutment of the bottom edge 202 of collar 107 with the top edge 204 of the nose member 116. According to embodiments of the present invention, the slider 110 is configured to slide along the slot 150 both before and after implantation of the suture anchoring system 100.

Collar 107 is slidably coupled with the implant body 210, the collar 107 includes one or more anchor fins 108, the collar 107 is slideable with respect to the implant body 210 between at least an implant position (as illustrated in solid lines in FIG. 2) in which the one or more anchor fins have a maximum lateral dimension D1 smaller than or the same as that of the insertion nose 116, and deployed position (illustrated partially in phantom lines in FIG. 2) in which the maximum lateral dimension D2 is larger than that of the insertion nose 116, according to embodiments of the present invention.

Figure 3:
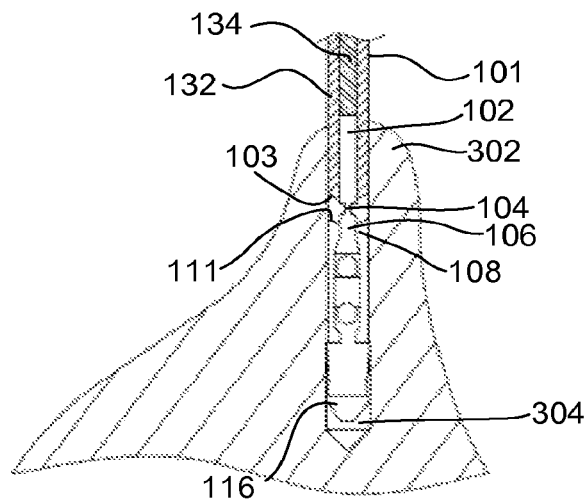
FIG. 3 illustrates a front cross sectional view of a suture anchor and inserter during installation in a bone hole, according to embodiments of the present invention.
Figure 4:
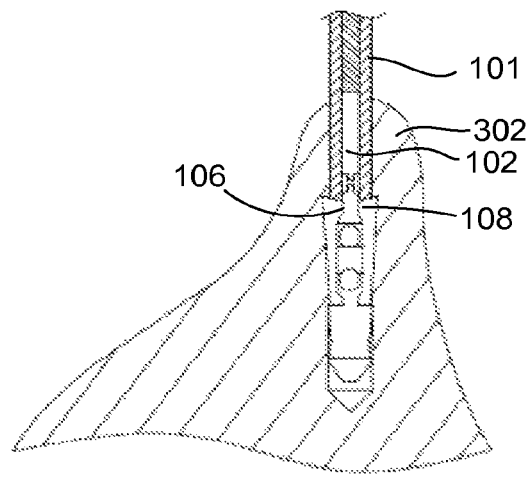
FIG. 4 illustrates a front cross sectional view of the suture anchor and inserter of FIG. 3 after activation of the spreader, according to embodiments of the present invention.
Figure 5:
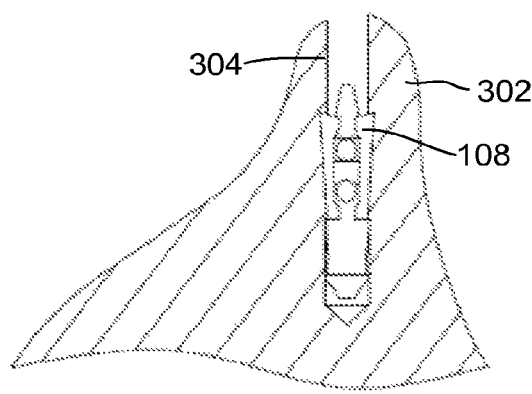
FIG. 5 illustrates a front cross sectional view of the suture anchor of FIGS. 3 and 4 after removal of the inserter, according to embodiments of the present invention.

FIGS. 3 through 5 illustrate a method for installing or implanting the anchor 100, according to embodiments of the present invention. The inserter attachment 102 attaches the implant body 210 with the inserter 101. The inserter 101 has an outer lateral dimension at its distal end 103 that is smaller than or the same as that of the insertion nose, the inserter 101 coupled to the inserter attachment 102 in a manner which permits actuation of the inserter 101 to slide the collar 107 with respect to the implant body 210. First, the suture anchor 100, which is attached to the inserter 101 via the inserter attachment 102, is placed within a hole 304 in the bone 302. In the non-deployed state, the anchor 100 and inserter 101 and fins 108 may be of a substantially uniform diameter and/or cylindrical shape to easily fit within the hole 304, as illustrated in FIG. 3, according to embodiments of the present invention. In some embodiments of the present invention, the hole 304 is pre-drilled. The inserter 101 may include a substantially hollow tube 132 at its distal end which contains and/or holds within it the inserter attachment 102, according to embodiments of the present invention.

According to some embodiments of the present invention, the inserter 101 comprises an outer shaft 132 and an inner shaft 134, wherein the outer shaft 132 slides with respect to the inner shaft 134, wherein the inner shaft 134 is rigidly coupled to the inserter attachment 102, and wherein the outer shaft 132 is configured to abut a proximal end 111 of the collar 107. According to other embodiments of the present invention, the inserter 101 comprises an outer shaft 132 only, which is configured to receive the inserter attachment 102, wherein the outer shaft 132 slides with respect to inserter attachment 102.

Once the anchor 100 and inserter 101 are placed within the bone hole 304, the inserter 101 is pushed in a distal direction, thereby permitting the distal end of the inserter 101 to contact the top of the collar 107. As illustrated in FIG. 4, continuing to push down on the collar 107 with inserter 101 and/or impulsing the inserter 101 onto the collar 107 causes the collar 107 to move in a distal direction with respect to the implant body 210, which causes the spreader 106 to expand or spread the fins 108 outwardly to engage the surrounding bone 302, according to embodiments of the present invention. Once the fins 108 of the collar 107 have been expanded, firmly engaging the suture anchor 100 with the surrounding bone 302, the inserter 101 may be pulled in a proximal direction to break the connection between the inserter 101 and inserter attachment 102 at detachment feature 104, as illustrated in FIG. 5, thus leaving the spreader 106 implanted in the bone 302. The inserter 101 and inserter attachment 102 may be connected in a way that permits the inserter 101 to slide distally over the inserter attachment 102, but which does not permit the inserter attachment 102 to fall out or off of the inserter 101 after the inserter attachment is broken from the spreader 106 at detachment feature 104, according to embodiments of the present invention.

According to some embodiments of the present invention, the inserter attachment 102 is detached at the detachment feature 104 while the inserter 101 is being pushed against the collar 107, rather than afterward. According to other embodiments of the present invention, the outer tube of the inserter 101 includes inwardly projecting teeth which slide easily over the detachment feature 104 in the distal direction, but which securely grasp the inserter attachment 102 at the detachment feature 104 when slid back in the proximal direction, thereby also retaining the inserter attachment 102 within the inserter 101 after the inserter attachment 102 has broken off at breakaway feature 104.

Although the detachment feature 104 is depicted as a set of notches on both sides of the inserter attachment 102, one of ordinary skill in the art will appreciate, based on the present disclosure, the structural weaknesses and/or various mechanisms that may be used to impart a breakaway or detachment performance at detachment feature 104 location. For example, the inserter attachment 102 may be connected to the spreader 106 at detachment feature 104 by a weak adhesive connection, a twisted connection, a twist-off connection, a precut connection, a perforated connection, a string connection, and/or the like, such that a force or action required to detach the inserter attachment 102 from the spreader 106 does not disturb or disengage the suture anchor 100.

The inserter 101 and/or insertion attachment 102 may also include graduations or other markings or registrations to assist the surgeon in achieving or evaluating the position and/or depth of the suture anchor 100, according to embodiments of the present invention.

Figure 6:
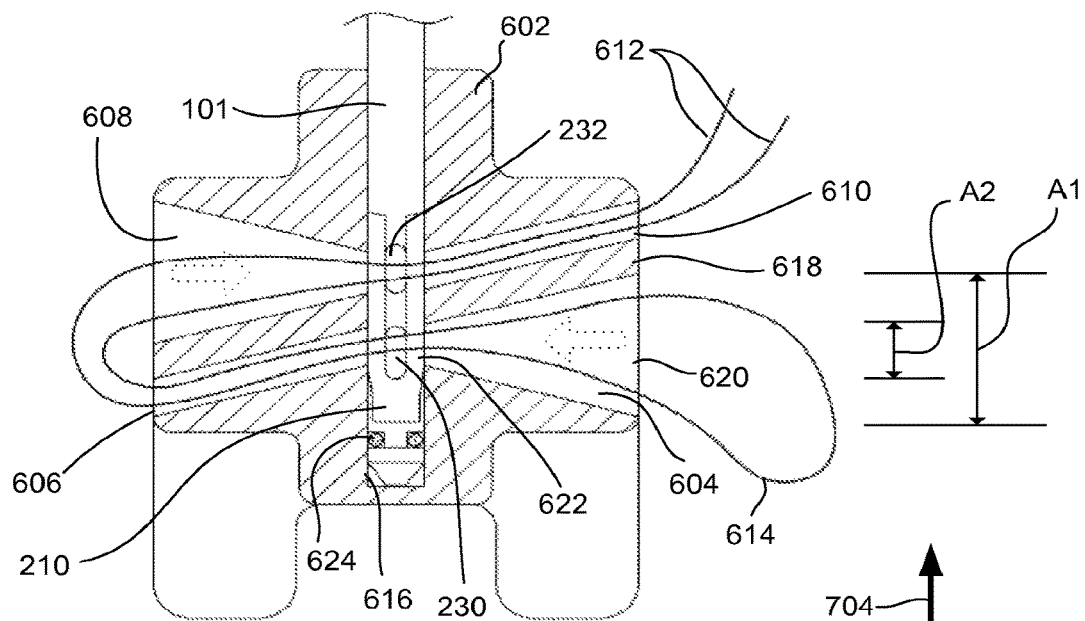
FIG. 6 illustrates a side cross sectional view of a suture anchor, inserter, and loader, with a knotless suture configuration, according to embodiments of the present invention.
Figure 7:
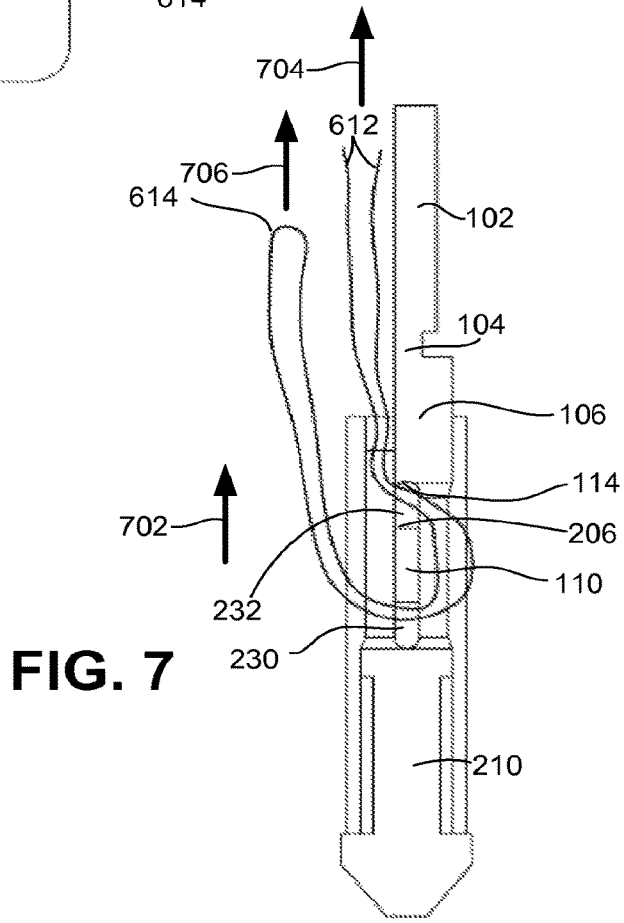
FIG. 7 illustrates a side cross sectional view of a suture anchor with a knotless suture configuration, according to embodiments of the present invention.

Prior to anchoring within bone 302, the suture anchor 100 may be loaded with suture in either a knotless fashion or a knotted fashion, according to embodiments of the present invention. FIGS. 6 and 7 illustrate loading of the suture anchor 100 in a knotless fashion. The suture illustrated in FIG. 6 is a double suture, or loop, having a looped end 614 and a pair of suture tails 612 at the other end, according to embodiments of the present invention. The looped end 614 may be looped through and/or attached to tissue or some other material that the surgeon will secure and/or place in tension with the suture, according to embodiments of the present invention.

The suture anchor 100 includes two apertures at least partially formed by the slider 110. As shown in FIG. 2, a first aperture 230 is formed at least partially by the distal end 112 of the notch in the implant body 210 and the distal (or bottom) end 208 of the slider 110. A second aperture 232 is formed at least partially by the proximal (or top) end 206 of the slider 110 and the proximal (or top) end 114 of the notch in the implant body 210, which is also the distal (or bottom) end 114 of the spreader 106, according to embodiments of the present invention.

Figure 17:
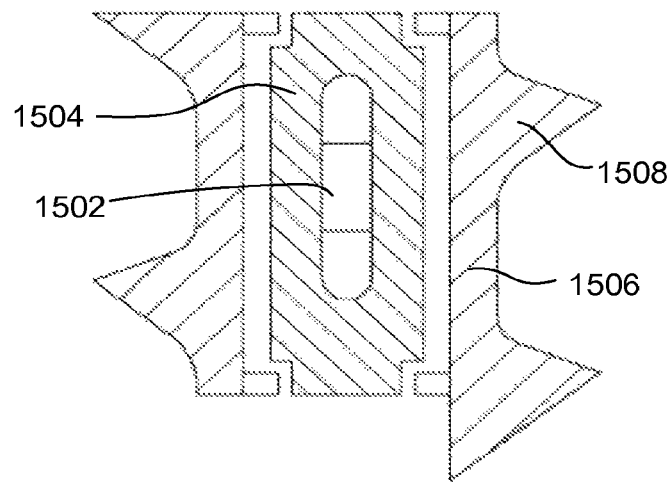
FIG. 17 illustrates a threaded anchor body that turns independently of a slider mechanism, according to embodiments of the present invention.

FIG. 6 illustrates the suture anchor 100 within a loader device 602 which facilitates loading the suture through apertures 230, 232 in the suture anchor 100. FIG. 17 also illustrates an inserter 101 with a loader 602 and implant 100 therein. A device like loader 602 reduces the time necessary to perform a given operation. The device 602 includes openings 604, 608 larger than the apertures 230, 232 in the suture anchor 100, to facilitate threading or loading of the suture through the suture anchor 100. The suture tails 612 are first placed through opening 604 in the loader 602, which narrows in size similar to a funnel and aligns with aperture 230 to pass the suture through the aperture 230 and out of the opening 606 on the other side of loader 602. The suture tails 612 are then placed through opening 608, which narrows in size and aligns with aperture 232 to pass the suture through the aperture 232 and out of opening 610 on the other side of loader 602. The loader 602 may then be removed from the suture anchor 100 and inserter 101, while leaving the suture threaded through apertures 230, 232. According to embodiments of the present invention, the loader 602 has two corresponding halves that open at a hinge, or that removably snap-fit together.

The loader 602 includes an inner cavity 616 configured to receive the distal end of the inserter 101 and the implant body 210, an outer surface 618, an opening 604 formed in the loader 602, the opening 604 extending from the outer surface 618 to the inner cavity 616, wherein the opening 604 has a first opening area 620 at the outer surface 618 and a second opening area 622 at the inner cavity 616, the first opening area 620 being larger than the second opening area 622, according to embodiments of the present invention. According to embodiments of the present invention, the area A1 of the first opening area 620 is at least twice as large as the area A2 of the second opening area 622. The loader 602 may also include an alignment feature configured to align one of the first and second apertures 230, 232 with the second opening area 622 when the distal end of the inserter 101 and the implant body 210 are received by the inner cavity 616. For example, one or more pin or ball members 624 may serve as alignment features, by interfacing with a slot on the implant body 210 or between implant body 210 and collar 107, to ensure that the position and orientation of the distal end of the inserter 101 and implant body 210 are known when received by the loader 602. For example, the alignment feature is a feature which aligns the first aperture 230 with the second opening area 622 when the anchor 100 is received by the loader 602, to permit easy threading of suture therethrough. Opening 608 may have characteristics similar to those of opening 604, according to embodiments of the present invention, but may be formed from an opposite side of the outer surface 618 as illustrated in FIG. 6.

FIG. 7 illustrates the suture anchor 100 after the suture has been loaded in a knotless configuration. If looped end 614 is connected to tissue and the suture anchor 100 is inserted within a bone hole and expanded as described with respect to FIGS. 3-5, the ends 612 may be pulled by the surgeon to tighten the tension on end 614. The tension on end 614 pushes the slider 110 in the direction indicated by arrow 702, which pinches or "cinches" or otherwise holds the suture between edge 114 of the implant body 210 and edge 206 of the slider 110, according to embodiments of the present invention. According to embodiments of the present invention, the harder the surgeon pulls ends 612, the tighter the suture is held between the slider 110 and the spreader 106. The slider 110 thus operates to permit the suture to slide through the suture anchor 100 when ends 612 are pulled in direction 704, while also prohibiting movement of the suture toward end 614 in direction 706, thereby inhibiting an unintended loosening of the tension on the tissue side 614 of the suture.

Although FIGS. 6 and 7 illustrate a suture loop, one of ordinary skill the art, based on the disclosure presented herein, will appreciate that the knotless configuration illustrated and described may similarly be achieved with multiple suture loops and/or a single non-looped suture strand, according to embodiments of the present invention. A suture loop may be loaded through the anchor 100 in the knotless configuration either before or after the suture has been passed through tissue, according to embodiments of the present invention. This knotless suture path also permits the surgeon to successively and selectively tighten the tension on end 614; for example, the surgeon may place a smaller amount of tension on end 614 by pulling suture tails 612 of the suture loop in direction 704, this smaller amount of tension being maintained by the locking mechanism of pinching between the slider 110 and the slot 150, and the surgeon may return later in the operation to add further tension to the end 614 by further pulling suture tails 612 in direction 704, and this may all be accomplished after implantation of the anchor 100.

Figure 8:
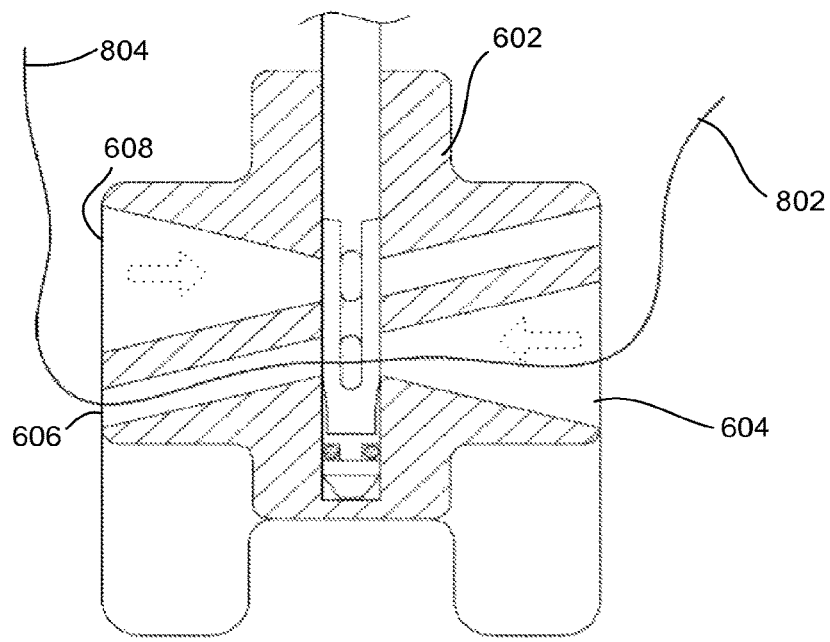
FIG. 8 illustrates a side cross sectional view of a suture anchor, inserter, and loader, with a knotted suture configuration, according to embodiments of the present invention.
Figure 9:
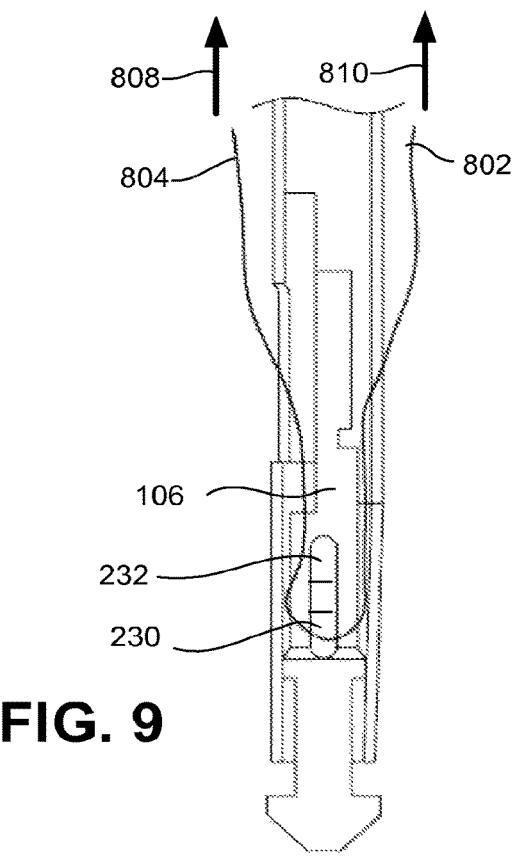
FIG. 9 illustrates a side cross sectional view of a suture anchor with a knotted suture configuration, according to embodiments of the present invention.

FIGS. 8 and 9 illustrate a loading of the suture anchor 100 for a knotted deployment. One end of the suture 802 may be attached to tissue or other material, and the other end 804 of the suture may be placed through opening 604, through aperture 230, and out of opening 606. The suture anchor 100 with the suture in a knotted configuration is illustrated in FIG. 9. The suture is able to slide freely back and forth through aperture 230, and may be placed through tissue or other material and knotted; for example, the two ends 802, 804 may be knotted together, according to embodiments of the present invention.

Although a single suture strand is illustrated, one of ordinary skill in the art, based on the present disclosure, will appreciate that multiple suture strands and/or looped suture strands may be loaded into the suture anchor 100 in a knotted configuration, according to embodiments of the present invention. According to an alternative embodiment of the present invention, loading the suture through the suture anchor 100 in a knotted configuration includes threading the suture through aperture 232 instead of aperture 230. According to embodiments of the present invention, the tension forces on the suture, in either the knotted or the knotless configurations, pull the implant body 210 proximally with respect to the collar 107, which serves to enhance and maintain the expansion of the collar 107 within the bone hole 304, promoting the continued secure anchoring of suture anchor 100 within bone hole 304.

Although the loader 602 is illustrated as being usable to load suture into the anchor 100 of FIGS. 1 and 2, different loaders 602 may have different dimensions in order to accommodate various different kinds of suture anchors having apertures formed by a slot and a slider. For example, a similar loader 602 may be used to facilitate loading of suture through the apertures of the anchors or locking mechanisms of FIGS. 12-18, with each loader having an inner cavity 614 sized to accept a particular anchor. Openings 604, 608 of the loader 602 may be substantially parallel to each other, may be separated by walls within the loader 602, and may have a circular, oval, rectangular, or other cross sectional shape, according to embodiments of the present invention. Openings 604, 608 facilitate suture passage, with or without a needle, according to embodiments of the present invention. According to some embodiments of the present invention, the inner cavity 614 has variable dimensions adapted to different implant models, which present varying dimensions. The loader 602 may have deformable and/or elastomeric walls which adapt to implants having different diameters, according to embodiments of the present invention.

In comparing FIGS. 7 and 9, because the slider 110 is configured to slide along the slot 150 both before and after implantation of the implant body 210, a suture passed through only one of the first and second apertures 230, 232 before implantation (see FIG. 9) is moveable freely in both directions 808, 810 (e.g. the suture travel directions achieved by pulling on either end of the suture) after implantation; while a suture threaded, before implantation, through one of the first and second apertures 230, around the slider 110, and back through the other of the first and second apertures 232 (see FIG. 7) is, after implantation, moveable freely in a first direction 704 but substantially inhibited from moving in a second direction 706 opposite the first direction. This inhibition of suture movement is caused in the knotless configuration because as end 614 is tensioned, the tension essentially applies an upward force to slider 110, which, in turn, pinches the suture between slider 110 and the upper edge of slot 150, according to embodiments of the present invention.

Figure 10:
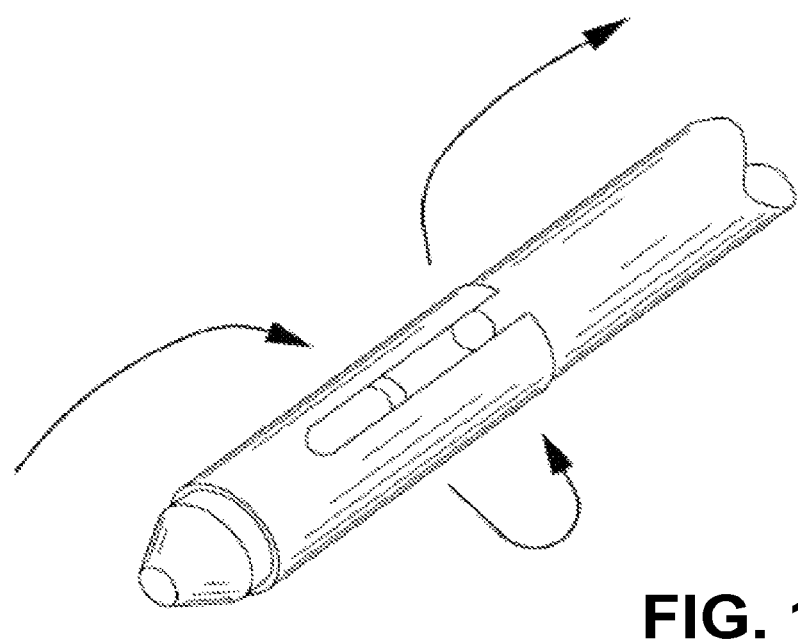
FIG. 10 illustrates a method for manually loading a suture into a suture anchor in a knotless configuration without a loader device, according to embodiments of the present invention.
Figure 11:
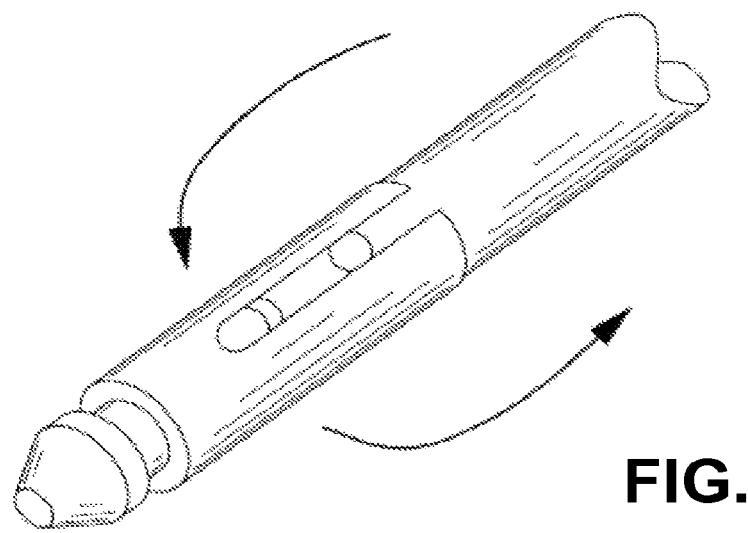
FIG. 11 illustrates a method for manually loading a suture into a suture anchor in a knotted configuration without a loader device, according to embodiments of the present invention.

Although a loader device 602 is illustrated for facilitating the loading or threading of the suture through one or more apertures 230, 232, one of ordinary skill in the art, based on the present disclosure, will appreciate that such loading may be accomplished by hand, without the assistance of a loader device, as illustrated in FIGS. 10 and 11.

Figure 12:
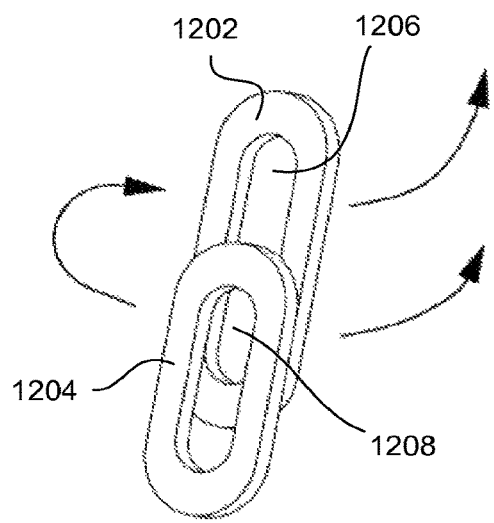
FIG. 12 illustrates a variation of a slider plate suture anchoring system illustrating a knotless suture loading configuration, according to embodiments of the present invention.
Figure 13:
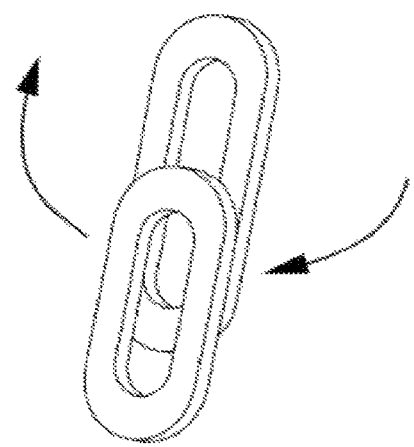
FIG. 13 illustrates a variation of a slider plate suture anchoring system illustrating a knotted suture loading configuration, according to embodiments of the present invention.
Figure 14:
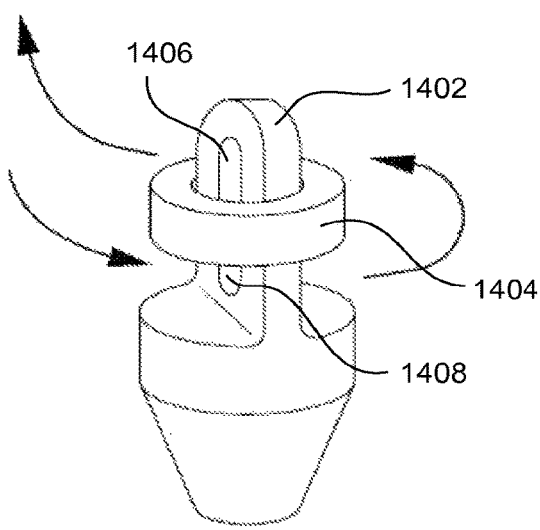
FIG. 14 illustrates a variation of a slider plate suture anchoring system illustrating a knotless suture loading configuration, according to embodiments of the present invention.
Figure 15:
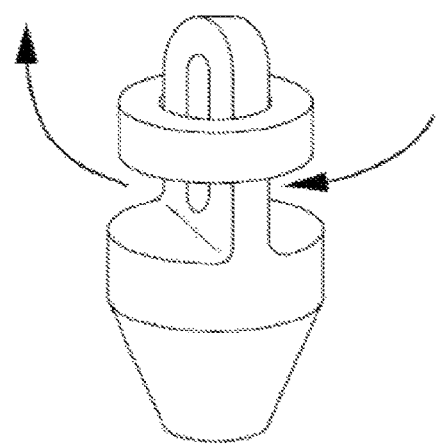
FIG. 15 illustrates a variation of a slider plate suture anchoring system illustrating a knotted suture loading configuration, according to embodiments of the present invention.

And although a slider 110 mechanism is illustrated, one of ordinary skill in the art, based on the present disclosure, will appreciate that other pinching or cinching mechanisms may be employed to secure the suture in the knotless configuration while also permitting threading of the suture in the knotted configuration, for example the cinch ring configuration illustrated in FIGS. 12 and 13 or the fixed eyelet and cross-piece configuration illustrated in FIGS. 14 and 15. In the ring cinch configuration of FIGS. 12 and 13, the longitudinal slot is formed by one ring 1202, and the other ring 1204 operates as a slider. In some embodiments, one of the rings 1202, 1204 may be rigidly coupled with the implant body, such as implant body 250; in other embodiments, both rings 1202, 1204 slide independently of one another and of the implant body. Sutures may be selectively threaded through apertures 1206, 1208 in a knotless configuration (as illustrated in FIG. 12), or in a knotted configuration (as illustrated in FIG. 13). In the configuration of FIGS. 14 and 15, the longitudinal element 1402 has a longitudinal slot formed therein, and the slider ring 1404 slides along element 1402 to separate the longitudinal slot into a first aperture 1406 and a second aperture 1408, which may be threaded in the knotless configuration (as illustrated in FIG. 14) or in the knotted configuration (as illustrated in FIG. 15), according to embodiments of the present invention. In either of the embodiments of FIGS. 12-15, the distal loop pulls upwardly against one of the two interacting elements to pinch or squeeze the suture between such element and the other element.

Figure 16:
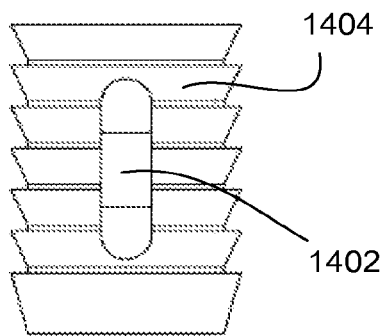
FIG. 16 illustrates a slider plate used with a pressure fit anchor body, according to embodiments of the present invention.
Figure 18:
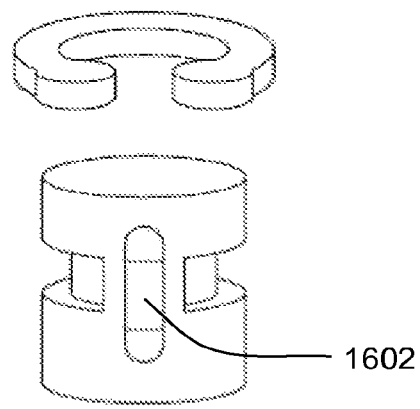
FIG. 18 illustrates a slider mechanism included in an expanding collar assembly, according to embodiments of the present invention.

A similar slider mechanism 110 may also be used with other implant bone fixation mechanisms; for example, a slider 1402 within a pressure fit fixation anchor body 1404 as illustrated in FIG. 16, or a slider 1502 within a fixture 1504 mounted within an outer anchor body 1506 with one or more threads 1508 which turns independently of the fixture 1504 and/or slider 1502 as illustrated in FIG. 17, or a slider 1602 within an expanding collar assembly as illustrated in FIG. 18, according to embodiments of the present invention. In each of these embodiments, the slider 1402, 1502, 1602 creates a proximal aperture and a distal aperture, and the free end of the suture may be loaded through the distal aperture and then through the proximal aperture to impart knotless performance, and can be loaded through the distal aperture only (or, alternatively, through the proximal aperture only) to impart knotted capability, according to embodiments of the present invention.

Figure 19:
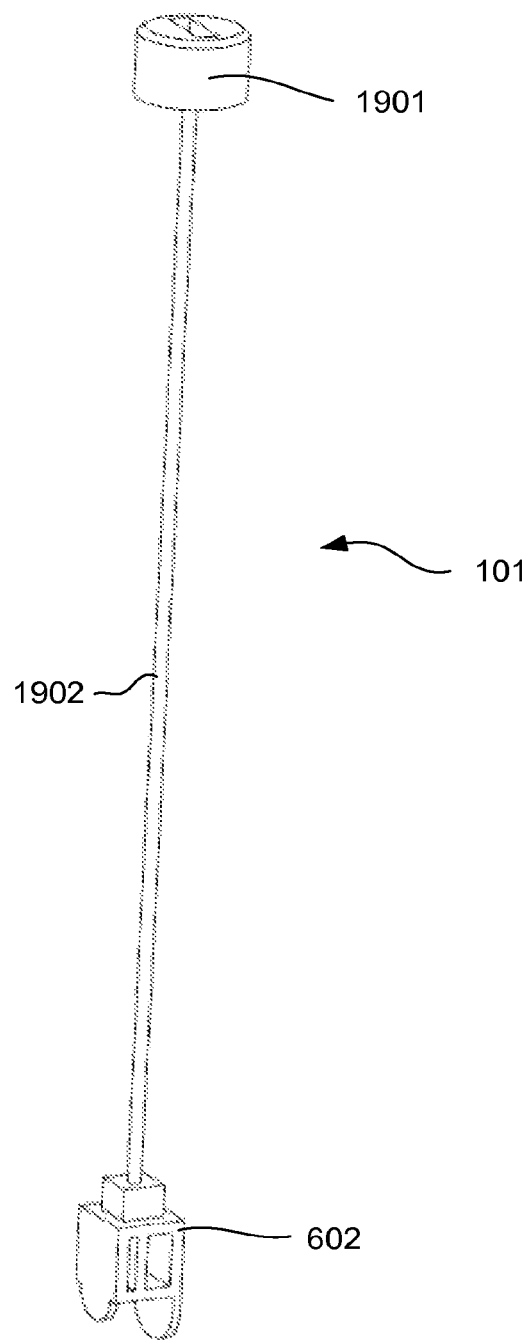
FIG. 19 illustrates an inserter coupled with a suture anchor implant and loader device, according to embodiments of the present invention.

FIG. 19 illustrates an inserter 101, according to embodiments of the present invention. A loader 602 is mounted on a distal end of the inserter 101, and the proximal end of the inserter 101 comprises a knob or handle 1901 which, along with the inserter shaft 1902, may be used by the surgeon to position, insert, and/or manipulate the implant 100 into the bone 320. The knob 1901 is adapted to include a grip that is practical and comfortable for the surgeon.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A suture anchoring system comprising:
a collar body extending along a longitudinal axis from a proximal end to a distal end, the collar body comprising:
a slot formed in the collar body, the slot extending through the collar body along an axis perpendicular to the longitudinal axis; and
a receiving slot formed in the collar body, the receiving slot configured to receive an implant body;
an implant body extending along the longitudinal axis when disposed within the receiving slot, the implant body comprising:
an implant body proximal portion and an implant body distal portion;
an opening formed in the implant body, the opening extending entirely through the implant body, the opening extending along an axis perpendicular to the longitudinal axis of the collar body when the implant body is disposed within the receiving slot, wherein the opening is positioned between the proximal end of the collar body and the distal end of the collar body when the implant body is disposed within the receiving slot,
wherein the implant body is configured to be moved toward the distal end of the collar body;
wherein the suture anchoring system comprises:
a first suture path at least partially formed by the slot and the implant body distal portion;
a second suture path at least partially formed by the slot and the opening formed in the implant body, the second suture path located proximally with respect to the first suture path;
wherein the suture anchoring system is configured such that movement of the implant body substantially inhibits movement of a suture threaded through the suture anchoring system.

2. The suture anchoring system of claim 1, wherein a proximal portion of the collar body is wider than a distal portion of the collar body near the distal end.

3. The suture anchoring system of claim 1, wherein the collar body comprises one or more anchor fins extending transverse to the longitudinal axis.

4. The suture anchoring system of claim 1, wherein the implant body has a tapered tip.

5. The suture anchoring system of claim 1, wherein the suture anchoring system is configured to pinch a suture at least in part with an edge of the implant body.

6. The suture anchoring system of claim 1, wherein when a suture is threaded through one of the first and second suture paths and back through the other of the first and second suture path, the suture moves freely in the first direction, but is pinched when moved in the second direction.

7. The suture anchoring system of claim 1, further comprising an inserter attachment coupled to the proximal end of the implant body with a break-away coupling.

8. The suture anchoring system of claim 1, wherein a portion of the implant body comprises a rectangular cross-section.

9. The suture anchoring system of claim 1, wherein a portion of the collar body comprises a taper.

10. The suture anchoring system of claim 1, wherein the distal end of the collar body is blunt.

11. The suture anchoring system of claim 1, wherein the receiving slot extends entirely through the collar body.

12. The suture anchoring system of claim 1, wherein the slot comprises a rounded edge.

13. The suture anchoring system of claim 1, wherein the implant body proximal portion contacts the receiving slot when the implant body is disposed within the receiving slot.

14. The suture anchoring system of claim 1, wherein the opening comprises a rounded edge.

15. The suture anchoring system of claim 1, further comprising the suture threaded through the suture anchoring system.

16. The suture anchoring system of claim 1, further comprising markings configured to assist a surgeon in evaluating a position or a depth of the suture anchoring system.

17. The suture anchoring system of claim 1, wherein the collar body comprises a rounded cross-section.

18. The suture anchoring system of claim 1, wherein the suture anchoring system is configured for installation in a bone hole.

19. The suture anchoring system of claim 1, wherein the suture anchoring system is configured for shoulder repair.

20. The suture anchoring system of claim 1, wherein at least a portion of the implant body extends beyond the proximal end of the collar body.

* * * * *